United States Patent
Breeuwer

(10) Patent No.: US 7,805,181 B2
(45) Date of Patent: Sep. 28, 2010

(54) NON-INVASIVE QUANTITATIVE MYOCARDIAL PERFUSION ASSESSMENT

(75) Inventor: Marcel Breeuwer, Eindhoven (NL)

(73) Assignee: Koninklijke Philips Electronics N.V., Eindhoven (NL)

(*) Notice: Subject to any disclaimer, the term of this patent is extended or adjusted under 35 U.S.C. 154(b) by 1199 days.

(21) Appl. No.: 10/562,892

(22) PCT Filed: Jun. 30, 2004

(86) PCT No.: PCT/IB2004/051069
§ 371 (c)(1), (2), (4) Date: Dec. 29, 2005

(87) PCT Pub. No.: WO2005/004066
PCT Pub. Date: Jan. 13, 2005

(65) Prior Publication Data
US 2006/0155185 A1    Jul. 13, 2006

(30) Foreign Application Priority Data
Jul. 1, 2003    (EP) .................................. 03101963

(51) Int. Cl.
*A61B 5/05* (2006.01)
(52) U.S. Cl. .................. 600/419; 382/128; 600/410; 600/411; 600/413; 600/420
(58) Field of Classification Search .............. 600/426, 600/410, 411, 413, 419, 420
See application file for complete search history.

(56) References Cited

U.S. PATENT DOCUMENTS

| | | | |
|---|---|---|---|
| 5,239,591 A | * | 8/1993 | Ranganath .................. 382/128 |
| 6,132,380 A | * | 10/2000 | Cohen et al. ................. 600/481 |
| 6,295,465 B1 | * | 9/2001 | Simonetti .................... 600/413 |
| 6,368,574 B1 | * | 4/2002 | Akeson et al. .............. 424/9.32 |
| 6,687,528 B2 | * | 2/2004 | Gupta et al. ................. 600/410 |

(Continued)

FOREIGN PATENT DOCUMENTS

EP    0543468 A1    5/1993

(Continued)

OTHER PUBLICATIONS

Xin Yang et al: Computer Aided Measurement of Local Myocardial Perfusion in MRI, IEEE Sep. 1993, pp. 365-368, XP101028755.

(Continued)

*Primary Examiner*—Brian Casler
*Assistant Examiner*—Parikha S Mehta

(57) ABSTRACT

In a computer-readable medium, device and method for quantitative assessment of cardiac perfusion, a myocardium is depicted on a series of cardiac images and is divided into image segments. A cardiac perfusion parameter is determined for each of the image segments. At least one image segment with a normal perfusion parameter value is selected. The cardiac perfusion parameters of the remaining image segments are normalized based on the normal perfusion parameter value of said image segment with normal perfusion. The perfusion parameter can be a maximum upslope of a time-intensity profile for distribution of a contrast agent in said myocardium. A normal maximum upslope is derived for at least one image segment with normal perfusion and a relative maximum upslope is calculated for each other segment with relation to the normal maximum upslope.

17 Claims, 4 Drawing Sheets

U.S. PATENT DOCUMENTS

| | | | |
|---|---|---|---|
| 7,333,845 B2* | 2/2008 | Hundley et al. | 600/407 |
| 2001/0000727 A1* | 5/2001 | Driehuys et al. | 424/9.36 |
| 2002/0095086 A1* | 7/2002 | Breeuwer | 600/426 |
| 2003/0065258 A1* | 4/2003 | Gupta et al. | 600/410 |
| 2004/0057607 A1* | 3/2004 | Breeuwer et al. | 382/128 |

FOREIGN PATENT DOCUMENTS

| | | |
|---|---|---|
| EP | 0543468 B1 | 5/1993 |

OTHER PUBLICATIONS

Nidal Al-Saadi, et al: Noninvasive Detection of Myocardial Ischemia From Perfusion Reserve Based on Cardiovascualar Magnetic Resonance, Circulation 2000; 101: pp. 1397-1383.

Norbert Wilke, et al: The Myocardial Perfusion Reserve: Assessment with Multisection, Quantitative, First-Pass MR Imaging, Radiology 1997, pp. 373-384.

* cited by examiner

NON-INVASIVE QUANTITATIVE MYOCARDIAL PERFUSION ASSESSMENT

This invention pertains in general to the field of image analysis and more particularly to image analysis of a series of non-invasively acquired cardiac images and even more particularly to the non-invasive assessment of perfusion of the myocardium by image analysis of a series of non-invasively acquired cardiac images.

The myocardium (MC) is the heart's muscular wall. It contracts to pump blood out of the heart, then relaxes as the heart refills with returning blood. Blood perfusion of the myocardium ensures functioning of the myocardium. Reduced blood perfusion of the myocardium is a cardiovascular disease. The quantitative assessment of myocardial perfusion is thus of importance for the diagnosis of this cardiac disease. Insufficient perfusion of the myocardium may be the result of the (partial) occlusion of a coronary artery, which is a disease called ischemia. Cardiac Magnetic Resonance Imaging (MRI) is becoming one of the preferred techniques for the diagnosis of this kind of cardiac disease. Myocardial perfusion is today calculated from first-pass myocardial perfusion images acquired with ECG-triggered contrast-enhanced MRI. Myocardial time-intensity profiles are measured from this series of cardiac images.

According to a method of quantification of myocardial perfusion, local myocardial time-intensity profiles are firstly measured from scans acquired when the heart was at rest and then when it was stressed. Perfusion is then quantified from these profiles. An example for a perfusion parameter thus derived is the so-called myocardial perfusion reserve index (MPRI), which has proven to be a good indicator of myocardial ischemia, as has been disclosed in Wilke at al., Radiology 1997; 204: pp. 373-384 and Al-Saadi et al., Circulation 2000; 101: pp. 1379-1383. The myocardial perfusion reserve index (MPRI) is defined as the maximum upslope of the time-intensity profile at stress divided by that of the time-intensity profile at rest. In order to normalize for the speed of injection of the contrast agent, the myocardial maximum upslopes are first divided by the maximum upslope of the time-intensity profile of the left ventricle (LV), when calculating myocardial perfusion parameters such as the MPRI. This time-intensity profile is usually called the LV input function.

Clinical validation has shown that the above described method may fail due to the fact that often only an insufficient LV input function is available and that therefore the maximum upslope of this LV function cannot be measured accurately. This occurs due to e.g. patient breathing or to non-linear behavior of the scanner at high image intensity levels, so that there is no linear relation between the increase in contrast agent in the LV and the increase in intensity in the perfusion images. As a result, the value of the calculated perfusion parameters, such as the MPRI, may not be very reliable or can even be completely wrong.

Therefore, a need exists for a reliable way of non-invasively quantitatively assessing myocardial perfusion independently of the relation between the increase in contrast agent in a ventricle and the increase in intensity in the myocardium in the perfusion images.

One object of the invention is to provide a reliable way of non-invasively quantitatively assessing myocardial perfusion. Another object is to provide a way of non-invasively quantitatively assessing myocardial perfusion independently of the relation between the increase in contrast agent in a ventricle and the increase in intensity in the myocardium in the perfusion images.

The present invention overcomes the above-identified deficiencies in the art and solves at least the above identified problems by providing a computer-readable medium, a device and a method for the quantitative assessment of cardiac perfusion according to the appended patent claims.

Cardiac perfusion is assessed by means of cardiac perfusion parameters, i.e. parameters that quantify the uptake of the contrast agent in the myocardium.

The general solution according to the invention is based on the fact that any myocardium contains parts that are normally perfused because otherwise the heart muscle would not be able to perform any pump action at all. More particularly, the perfusion in these normally perfused parts is taken as a reference of the speed of contrast medium injection, instead of deriving this information from e.g. the LV time-intensity profile.

According to aspects of the invention a computer-readable medium, a device and a method for the quantitative assessment of cardiac perfusion are disclosed.

According to one aspect of the invention a computer-readable medium is provided, which stores a computer program for the non-invasive quantitative assessment of cardiac perfusion from a series of cardiac images, such as a $1^{st}$-pass perfusion image series. This computer program is in use processed by a computer and has a plurality of code segments, wherein a first code segment selects one or more segments with normal perfusion, such that cardiac perfusion parameters of the remaining image segments are based on a perfusion parameter of said image segment(s) with normal perfusion. According to embodiments of the invention, further code segments divide the myocardium depicted on the image series into segments, a time-intensity profile for distribution of a contrast agent in the myocardium is determined for each of these segments, and a maximum upslope for each time-intensity profile of myocardium image segments is determined. Furthermore, a normal maximum upslope is derived and a relative maximum upslope is calculated for each segment.

According to another aspect of the invention an apparatus is provided, wherein said apparatus comprises means for executing the above computer program.

According to a further aspect of the invention, a method for the quantitative assessment of cardiac perfusion from a non-invasively captured series of cardiac images, such as a $1^{st}$-pass perfusion image series is provided. The method comprises the step of selecting at least one segment with normal perfusion, such that cardiac perfusion parameters of the remaining image segments are based on a perfusion parameter of said image segment(s) with normal perfusion. According to embodiments, the method further comprises dividing a myocardium depicted on the series of cardiac images into image segments. In a further step, a time-intensity profile for distribution of a contrast agent in said myocardium is determined for each of said image segments. Then a maximum upslope for each time-intensity profile is determined. Subsequently a normal maximum upslope is derived and a relative maximum upslope is calculated for each image segment.

The present invention has the advantage over the prior art that it reduces errors in cardiac perfusion measurement due to e.g. breathing artefacts and/or non-linear scanner behavior.

For example, the computer-readable medium comprises a code segment for thresholding said N highest perfusion parameter values. Notably, the series of cardiac images is series of first-pass myocardial perfusion images. For example, said image segment is at least one image pixel.

According to an aspect of the invention, the method comprises dividing a myocardium depicted on said cardiac image series into image segments, determining a time-intensity profile for distribution of a contrast agent in said myocardium for each of said image segments, determining said perfusion parameter for each time-intensity profile, deriving a normal perfusion parameter, and calculating a relative perfusion parameter with relation to said normal perfusion parameter for each of said image segments.

A ratio is calculated of myocardial perfusion parameters derived at stress and myocardial perfusion parameters derived at rest for each image segment. E.g. said ratio is a MPRI calculated as a ratio from relative maximum upslopes derived at rest and at stress. Good results are achieved when said perfusion parameter is a maximum upslope of a time-intensity for distribution of a contrast agent in a myocardium comprising said image segments. Notably, said assessment of cardiac perfusion is used for the diagnosis of cardiac diseases. Notably, a workstation is used for performing the method according to the invention.

Further objects, features and advantages of the invention will become apparent from the following description of embodiments of the present invention, reference being made to the accompanying drawings, in which.

Figure 1:
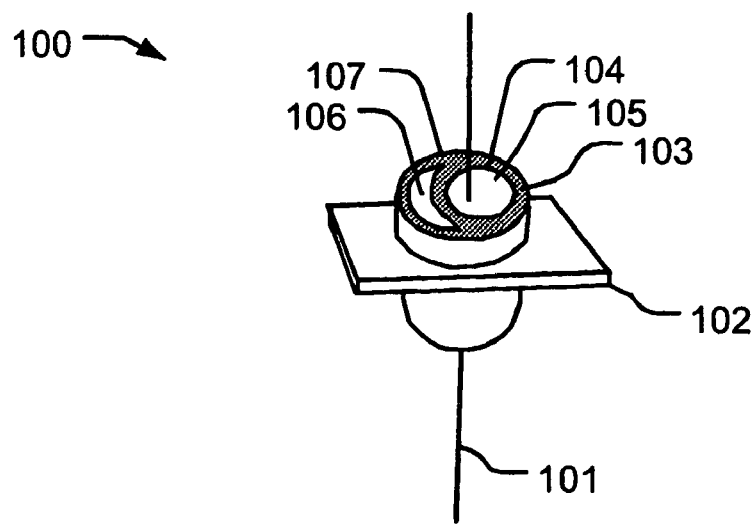
FIG. 1 is a perspective view schematically illustrating the term "short axis"
Figure 2:
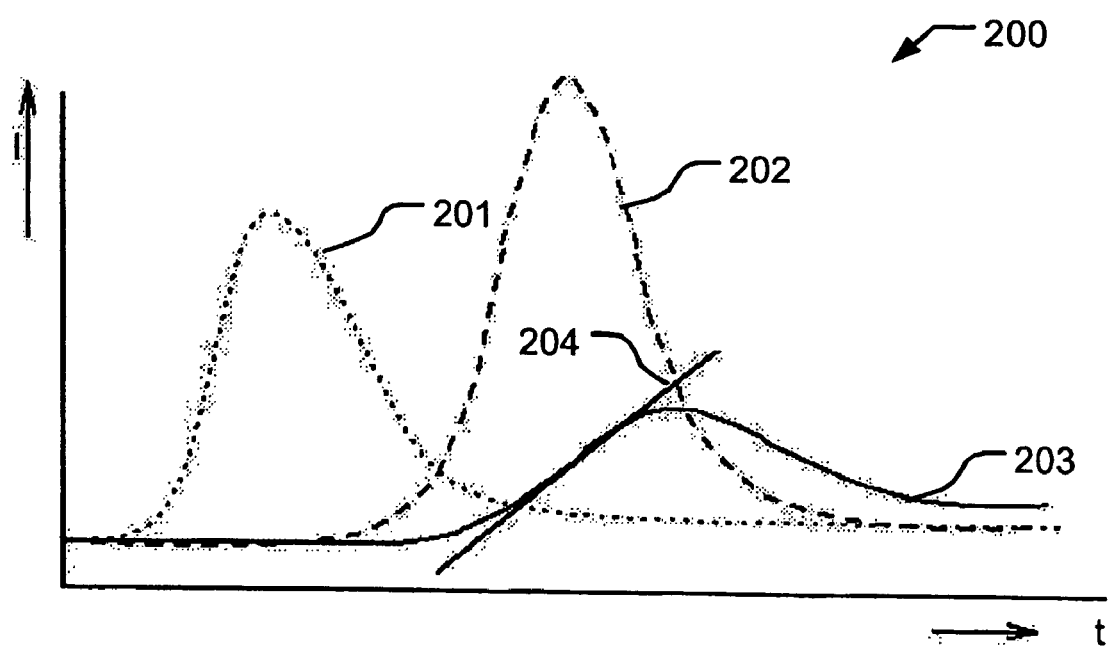
FIG. 2 is a graph illustrating the intensity progress as a function of time of different cardiac regions (the time-intensity profile)

MR cardio perfusion scans are obtained by recording a number of short-axis slices during a period of 20 to 40 seconds. The definition of a short-axis slice is illustrated in FIG. 1, wherein a long axis 101 and a short-axis slice 102 are shown. Furthermore the schematic illustration of cardiac components 100 shows the left ventricle 105, the right ventricle 106, the myocardium 103, the epicardial contour 107 and the endocardial contour 104. The acquisition of the cardio perfusion scans is ECG controlled so that each set of slices represents the same phase of the heart cycle, usually starting from end diastole. A few seconds after the beginning of the scan, a contrast agent is injected into the patient and subsequently the heart is imaged. The heart is also imaged in the period prior to the injection of the contrast agent, to acquire so called baseline images. These baseline images are sometimes used to correct for intensity inhomogeneity. The contrast agent shows brightly in the MR images. In a MR $1^{st}$-pass perfusion image series, it is observed that the contrast agent first enters the right ventricle (RV), then the left ventricle (LV) and finally the myocardium (MC). The intensity I as a result of the contrast agent as a function of time t of a segment in the RV, the LV and the MC is shown in graph 200 in FIG. 2.

Figure 3A:
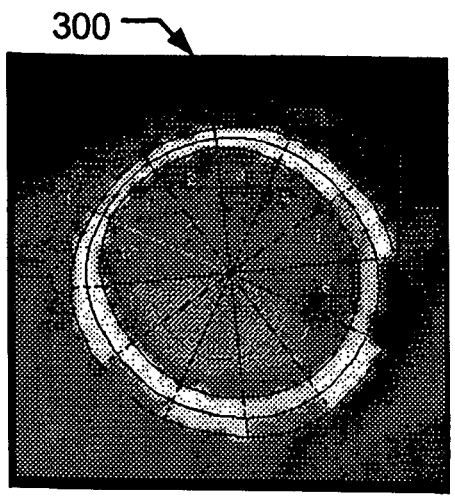
FIG. 3A is an exemplary cardiac MR image showing cardiac segments with the relative maximum upslopes at rest.
Figure 3B:
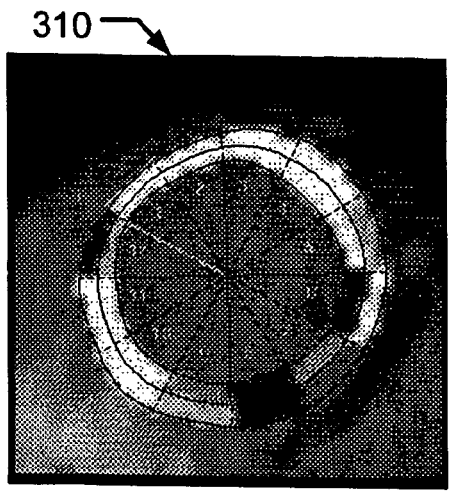
FIG. 3B is an exemplary cardiac MR image showing cardiac segments with the relative maximum upslopes at stress.

Firstly the contrast agent is spread in the RV, as shown by the intensity increase of the dotted curve 201, which represents the RV bolus. Then the contrast agent is spread in the LV, as shown by the intensity increase of the dashed curve 202, which represents the LV bolus. The spreading of the contrast agent in the MC, is shown by the solid curve 203 and the maximum upslope is indicated with the straight line 204. The myocardial perfusion reserve index (MPRI) is defined as the maximum upslope of the time-intensity profile at stress divided by that of the time-intensity profile at rest. In order to normalize for the speed of injection of the contrast agent, the myocardial maximum upslopes are according to the prior art first divided by the maximum upslope of the time-intensity profile of the left ventricle (LV). As mentioned above, this is not always reliable. An exemplary image illustrating this problem is shown in FIGS. 3A and 3B.

Since the signal in the myocardium may be very noisy, generally the myocardium is divided into segments and the intensity measurements are averaged over these segments. These segments generally coincide with areas of the myocardium, which are supplied with blood from a certain coronary artery. In this way, if a reduced perfusion is observed in a myocardial segment, it can be traced back to the supplying artery. Depending on the level of noise in the images, this myocardial segment consists of at least one image pixel. Cardiac images having a sufficiently low noise level, allow assessment of myocardial perfusion at the pixel level.

Quantitative perfusion analysis is performed by using the normalized upslope of the myocardial signal enhancement to derive the myocardial perfusion parameters or indexes, such as the myocardial-perfusion reserve index.

Figure 5:
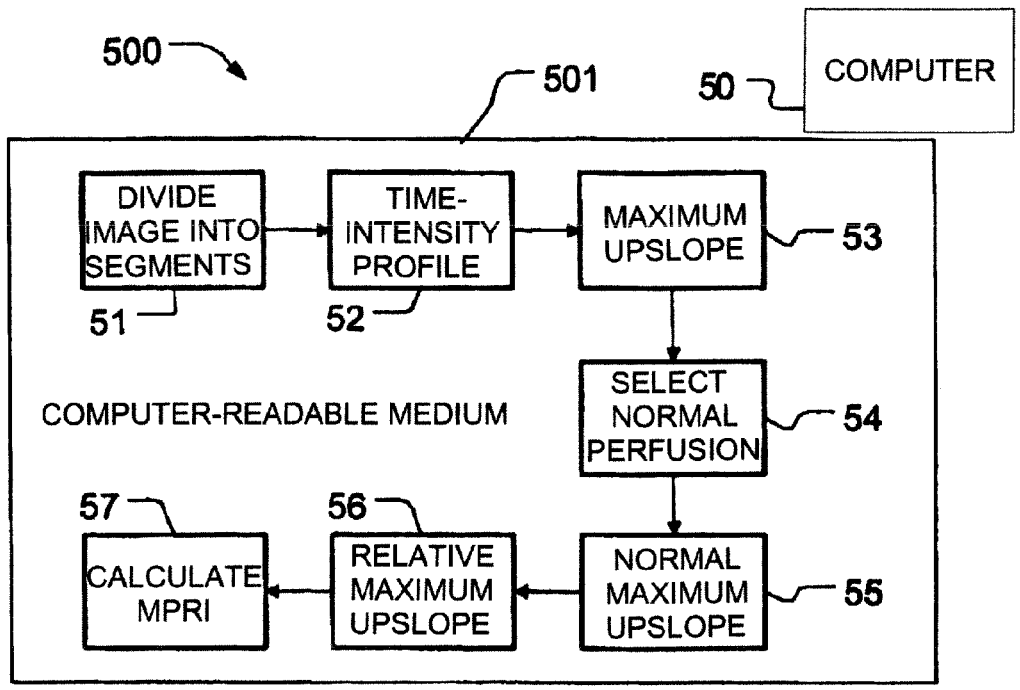
FIG. 5 is a schematic diagram showing a computer-readable medium according to an embodiment of the invention.

In an embodiment of the invention according to FIG. 5, a computer readable medium 500 stores a computer program 501 for the non-invasive quantitative assessment of cardiac perfusion from a cine series. This computer program is in use processed by a computer 50 and has a plurality of code segments 51-57, wherein a first code segment 51 divides a myocardium depicted on the cine series into segments. A second code segment 52 determines a time-intensity profile for distribution of a contrast agent in said myocardium for each of said segments. Then a third code segment 53 determines a maximum upslope for each time-intensity profile and a fourth code segment 54 selects one or more segments with normal perfusion. A fifth code segment 55 derives subsequently a normal maximum upslope and a sixth code segment 56 calculates a relative maximum upslope for each segment. Finally a seventh code segment 57 calculates the myocardial perfusion reserve index (MPRI) for each segment from a ratio of relative maximum upslopes derived at rest and at stress.

Figure 6:
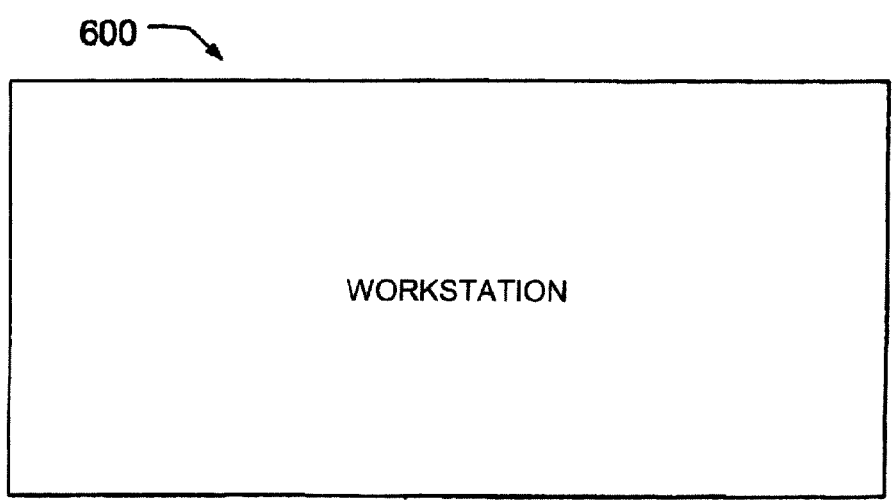
FIG. 6 is a schematic diagram showing a device according to an embodiment of the invention.

A further embodiment of the invention is illustrated in FIG. 6, wherein a workstation 600 is provided for executing the above computer program 501.

Figure 7:
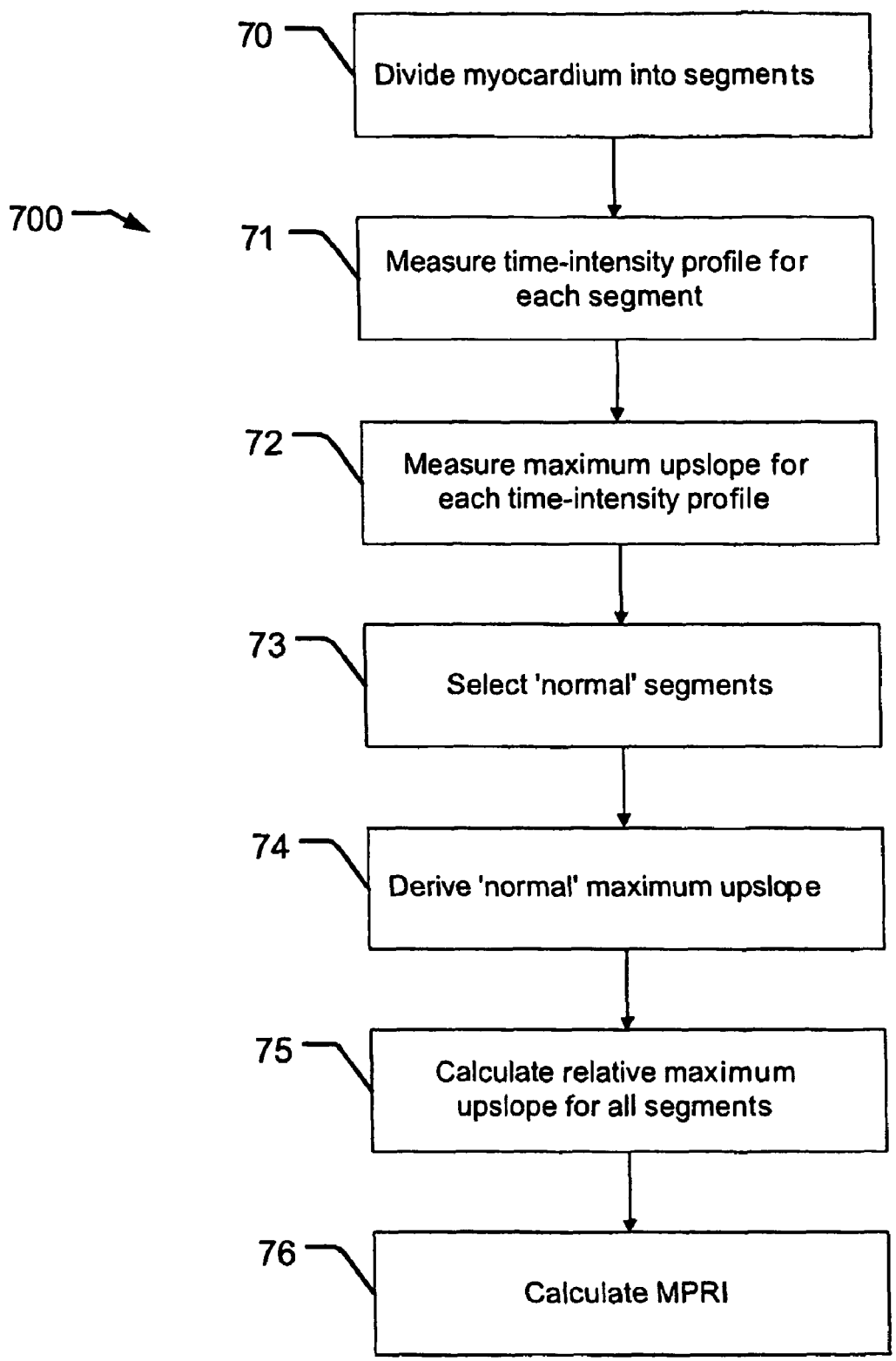
FIG. 7 is a flow chart illustrating a method for the assessment of cardiac perfusion according to an embodiment of the invention.

In another embodiment of the invention according to FIG. 7, a method 700 for quantitative assessment of cardiac perfusion from cine series is shown. The method 700 comprises the following steps and starts with the step 70 by dividing the myocardium into small segments. Then the myocardial time-intensity profile is measured in each segment according to the next step 71. In the subsequent step 72 the maximum upslope is measured for each time-intensity profile of the segments. Subsequently one or more 'normal' segments are automatically selected in step 73 and a 'normal' maximum upslope value is derived from the selected 'normal' segments in step 74. The maximum upslopes of all other segments are then expressed as a percentage of the normal maximum upslope, which henceforth will be called the 'relative maximum upslope', according to step 75. Finally, in step 76, the MPRI is calculated as the ratio of the relative maximum upslopes at stress and at rest.

The normal segment(s), may be chosen according to criteria such as:

the segment with the highest maximum upslope, the average of N segments with the N highest maximum upslopes, e.g. N=3 for a division of the myocardium into 24 segments, the average of N segments with the N highest maximum upslopes, but excluding those that have an upslope below a certain threshold in order to avoid inclusion of ischemic segments.

Using the first example, the highest upslope is taken as a reference, which means that the relative upslopes of all other segments are always below 100%. Furthermore, the MPRI is never much larger than 1.0. In fact, values around 1.0 indicate myocardial tissue that is well perfused both at rest and at stress, whereas significantly lower values indicate potentially ischemic tissue, which is not sufficiently perfused at stress.

Figure 4A:
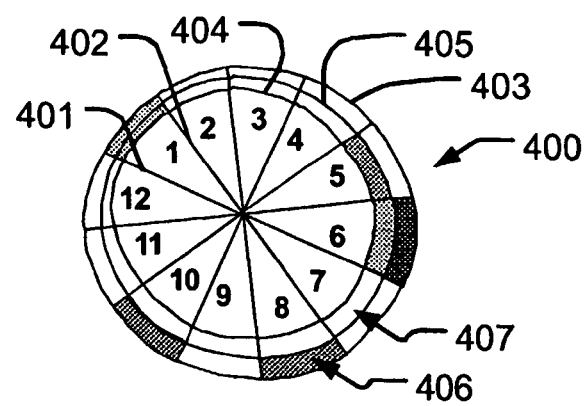
FIGS. 4A and 4B are a schematic illustration of FIGS. 3A and 3B respectively.
Figure 4B:
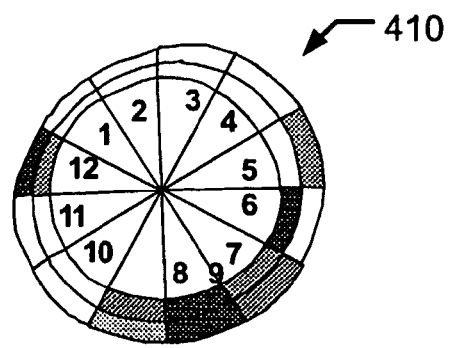

FIGS. 3A, 3B, 3C, 4A and 4B show an illustrative example of performing an embodiment of the invention. FIGS. 3A and 3B show two exemplary first-pass myocardial perfusion images, wherein the images are divided into image segments and the relative maximum upslopes at rest and at stress are respectively indicated in the images. FIG. 3A shows the maximum upslope at rest. FIG. 3B shows the maximum upslope at stress. The magnitude of the maximum upslope is coded by means of different grey levels in the images, wherein black corresponds to low values of the maximum upslope and white corresponds to high values of maximum upslope. Greyscale values between black and white indicate maximum upslope values between these extreme values. FIGS. 4A and 4B are schematic illustrations of FIGS. 3A and 3B respectively. The cardiac images 300, 310, 320, 400, 410 are divided into exemplary twelve sectors 1-12 delineated by lines 401, 402. The myocardium is delineated by concentric contour lines 403, 404 and subdivided by a concentric line 405. In this way the myocardium depicted on the images is divided into segments 406, 407. For these exemplary segments, a perfusion parameter is calculated, and may be visualized by means of greyscale coding, as in FIGS. 3A, 3B, 4A and 4B, or by means of other appropriate coding methods, such as color coding.

Figure 3C:
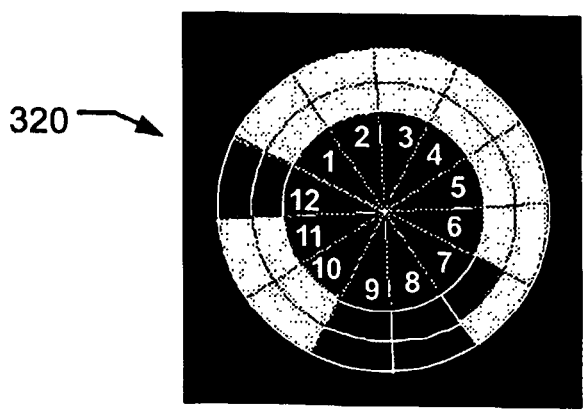
FIG. 3C is a schematic illustration of the thresholded MPRI corresponding to FIGS. 3A and 3B.

FIG. 3C shows a schematic illustration of the thresholded MPRI corresponding to FIGS. 3A and 3B as well as FIGS. 4A and 4B. In the example of FIG. 3C, a white segment indicates that the MPRI is above a certain, e.g. 75%, and a black segment indicates that the MPRI is below said threshold.

These patient images cannot be analyzed in the conventional way due to the low quality of the LV input function. According to FIG. 3C, the MPRI calculated with the novel method clearly shows a large insufficiently perfused area at the bottom as well as two smaller areas on the right and left side.

Applications and use of the above described computer readable medium, device, and method according to the invention are various and include exemplary fields such as detection of normal, ischemic and infarcted myocardial tissue using non-invasive medical imaging.

The present invention has been described above with reference to specific embodiments. However, other embodiments than the preferred above are equally possible within the scope of the appended claims, e.g. different ways of determining 'normal' myocardial segments than those described above, performing the above method by hardware or software, etc. The invention is further not limited to a certain imaging technique. Generally the cine sequences used for analysis by the invention may be captured by any suitable medical imaging technique, i.e. any imaging technique for imaging inside parts of a mammal body providing suitable cardiac cine sequences. These imaging techniques comprise Magnetic Resonance (MR), Computer Tomography (CT), Nuclear Medicine (NM) and Ultrasound (US) Imaging.

The described computer program, method and device are not limited to myocardial segments consisting of a certain number of pixels. Provided that the image quality is sufficient, the computer program, method and device work on pixel level. Instead of choosing "normal" segments, "normal" pixels, etc. are chosen.

The present invention is also not limited to specific myocardial perfusion parameters, but may be used for derivation of any myocardial perfusion parameter or myocardial perfusion indexes. The present invention has been described above with reference to specific embodiments and calculation of a MPRI for myocardial assessment. An example of another relevant parameter, which may be assessed by the present invention, is the accumulated inflow. The accumulated inflow is sometimes also called the area under the time-intensity profile curve, which can be calculated by integrating the segmental time-intensity profile in a certain time window, e.g. the period during which the contrast agent passes the myocardium for the first time.

Furthermore, the term "comprises/comprising" when used in this specification does not exclude other elements or steps, the terms "a" and "an" do not exclude a plurality and a single processor or other units may fulfill the functions of several of the units or circuits recited in the claims.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A non-transitory computer-readable medium for storing thereon a processor-executable computer program for non-invasive quantitative assessment of cardiac perfusion from a series of cardiac images comprising image segments, said computer program including one or more code segments which:

select at least one image segment with normal perfusion;

determine a maximum upslope of the at least one selected image segment with normal perfusion;

determine a maximum upslope of image segments without normal perfusion; and normalize the maximum upslope of the image segments without normal perfusion using the maximum upslope of the at least one image segment with normal perfusion such that cardiac perfusion parameters of the segments without normal perfusion are based on a cardiac perfusion parameter of said at least one image segment having normal perfusion.

2. The computer-readable medium according to claim 1, further comprising code segments for:

dividing a myocardium depicted on said cardiac image series into said image segments, determining a time-intensity profile for distribution of a contrast agent in said myocardium for each of said image segments, and determining said perfusion parameter for each of said time-intensity profiles of said image segments.

3. The computer-readable medium according to claim 1, said computer program further comprising a code segment for:
calculating a ratio of cardiac perfusion parameters derived at stress and cardiac perfusion parameters derived at rest for each image segment.

4. The computer-readable medium according to claim 3, wherein said ratio of cardiac perfusion parameters is a myocardial perfusion reserve index (MPRI).

5. The computer-readable medium according to claim 4, wherein said MPRI is calculated from relative maximum upslopes derived at rest and at stress.

6. The computer-readable medium according to claim 3, wherein said ratio of cardiac perfusion parameters is a thresholded MPRI being calculated by thresholding a ratio calculated from relative maximum upslopes derived at rest and at stress.

7. The computer-readable medium according to claim 1, wherein the one or more code segments further:
generate a display of said perfusion parameter for visualizing insufficiently perfused myocardial areas.

8. The computer-readable medium according to claim 1, wherein said one or more code segments further selects an image segment with the highest perfusion parameter value of all image segments as the image segment having normal perfusion, wherein a high perfusion parameter value is defined as good perfusion.

9. The computer-readable medium according to claim 1, wherein normalizing the maximum upslope of the image segments without normal perfusion includes:
determining relative maximum upslopes of the image segments without normal perfusion as a percentage of the maximum upslope of the at least one image segment with normal perfusion.

10. The computer-readable medium according to claim 1, wherein the one or more code segments further: calculate the relative maximum upslope for each of the image segments as a percentage of the maximum upslope of the at least one image segment with normal perfusion.

11. A non-transitory computer-readable medium for storing thereon a processor executable computer program for non-invasive quantitative assessment of cardiac perfusion from a series of cardiac images comprising image segments, said computer program including one or more code segments which:
select at least one image segment with normal perfusion, including selecting an average metric calculated from N image segments with N highest perfusion parameter values, wherein N is an integer number significantly lower than the total number of image segments, such that cardiac perfusion parameters of the remaining image segments are based on a cardiac perfusion parameter of said at least one image segment having normal perfusion.

12. A workstation configured for quantitative assessment of cardiac perfusion, said workstation comprising:
a processor programmed to:
receive a series of cardiac images which carry perfusion information;
segment the cardiac images into a plurality of image segments;
determine a maximum upslope for each image segment;
identify at least one image segment with a highest maximum upslope, the one or more image segments with the highest maximum upslope being deemed to have normal perfusion; determine relative maximum upslope for image segments without normal perfusion as a percentage of the maximum upslope of the at least one image segment with the highest maximum upslope to generate a cardiac perfusion parameter for the image segments without normal perfusion;
a display unit which generates a display indicative of the generated cardiac perfusion parameters.

13. A method for quantitative assessment of cardiac perfusion from a non-invasively captured cardiac series of cardiac images comprising image segments, the method executed by a processor and comprising:
selecting at least one image segment with normal perfusion; and
determining relative cardiac perfusion parameters of remaining image segments based on a cardiac perfusion parameter of said image segment with normal perfusion, wherein the determining of the relative cardiac perfusion parameters includes:
determining a maximum upslope for each of the remaining image segments;
determining a maximum upslope of the image segment with normal perfusion; and
calculating the maximum upslope for each of the remaining image segments as a percentage of the upslope for the image segment with normal perfusion to generate the relative perfusion parameter generating a display indicative of the relative perfusion parameter on a display monitor.

14. The method according to claim 13, wherein determining the relative perfusion parameters with a processor includes:
determining a perfusion parameter for each of the remaining image segments;
normalizing the determined perfusion parameter of each remaining segment with the perfusion parameter of the image segment with normal perfusion.

15. The method according to claim 13, further including: storing the relative perfusion parameter.

16. An apparatus for non-invasive qualitative assessment of cardiac perfusion, comprising:
a processor programmed to:
(a) segment a series of cardiac images into a series of image segments of a myocardium;
(b) choose at least one of the image segments with a higher contrast agent uptake rate as a segment with normal perfusion;
(c) identify image segments with lower contrast agent uptake rates than the segments with the normal perfusion as segments with below normal perfusion;
(d) generate a perfusion parameter for segments with below normal perfusion;
(e) generate a perfusion parameter for the at least one of the image segments with normal perfusion; and
(f) normalize the below normal perfusion parameter in accordance with normal perfusion parameter;
(g) wherein steps (a)-(f) are performed on cardiac images in a stress state and in a rest state.

17. The apparatus according to claim 16, wherein the at least one segment with normal perfusion is chosen according to criteria including at least one of:
an image segment with a highest maximum upslope,
an average of N segments with the highest maximum upslope, where N is an integer greater than 1,
an average of N segments which both exceed a selected threshold and have the highest maximum upslope.

* * * * *